US010791993B2

(12) United States Patent
Steiger et al.

(10) Patent No.: US 10,791,993 B2
(45) Date of Patent: Oct. 6, 2020

(54) METHOD AND DEVICE FOR ANALYZING CONTINUOUSLY MONITORED PHYSIOLOGICAL MEASUREMENT VALUES OF A USER

(71) Applicant: Roche Diabetes Care, Inc., Indianapolis, IN (US)

(72) Inventors: Bernd Steiger, Roemerberg (DE); Jürgen Rasch-Menges, Schwetzingen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 166 days.

(21) Appl. No.: 15/166,413

(22) Filed: May 27, 2016

(65) Prior Publication Data
US 2016/0270737 A1   Sep. 22, 2016

Related U.S. Application Data

(63) Continuation of application No. PCT/EP2014/075833, filed on Nov. 27, 2014.

(30) Foreign Application Priority Data

Nov. 28, 2013  (EP) .................................... 13194952

(51) Int. Cl.
*A61B 5/00*  (2006.01)
*A61B 5/145*  (2006.01)
(Continued)

(52) U.S. Cl.
CPC ........ *A61B 5/7275* (2013.01); *A61B 5/14532* (2013.01); *A61B 5/4842* (2013.01);
(Continued)

(58) Field of Classification Search
CPC .............. A61B 5/14532; A61B 5/7275; A61B 2560/0247; A61B 5/7246; G16H 50/20
See application file for complete search history.

(56) References Cited

U.S. PATENT DOCUMENTS

2007/0032706 A1*  2/2007  Kamath .................... A61B 5/01
                                                        600/300
2009/0105573 A1*  4/2009  Malecha ................ G16H 50/50
                                                        600/365
(Continued)

FOREIGN PATENT DOCUMENTS

CN       101594820 A      12/2009
CN       102740770 A      10/2012
(Continued)

OTHER PUBLICATIONS

International Preliminary Report on Patentability and Written Opinion of the International Searching Authority, PCT/EP2014/075833, dated Mar. 14, 2016.

*Primary Examiner* — Christian Jang
*Assistant Examiner* — Karen E Toth
(74) *Attorney, Agent, or Firm* — Bose McKinney & Evans LLP (57) ABSTRACT

The application relates to a method for analyzing continuously monitored physiological measurement values of a user, the method being performed in a data processing system and comprising: providing, by a data interface, a set of present physiological measurement values, determining whether a common pattern of values is contained in both the set of present physiological measurement values and a set of historical physiological measurement values, if the common pattern of values is found, requesting the user to provide contextualization for at least the present physiological measurement values of the common pattern of values, receiving contextualization and storing contextualized data. Further- (Continued)

more, the application relates to a device for analyzing continuously monitored physiological measurement values of a user.

15 Claims, 2 Drawing Sheets

(51) Int. Cl.
  *G16H 50/20* (2018.01)
  *G16H 50/70* (2018.01)

(52) U.S. Cl.
  CPC ............ *A61B 5/7246* (2013.01); *A61B 5/743* (2013.01); *A61B 5/7475* (2013.01); *G16H 50/20* (2018.01); *A61B 5/6898* (2013.01); *G16H 50/70* (2018.01)

(56) References Cited

U.S. PATENT DOCUMENTS

| | | | | |
|---|---|---|---|---|
| 2009/0271729 | A1* | 10/2009 | Killoren Clark ... | G06F 19/3418 715/771 |
| 2011/0160555 | A1* | 6/2011 | Reifman ............ | A61B 5/14532 600/365 |
| 2012/0165638 | A1* | 6/2012 | Duke ................. | A61B 5/14532 600/365 |
| 2012/0232520 | A1 | 9/2012 | Sloan et al. | |
| 2012/0289788 | A1* | 11/2012 | Jain .................... | G06F 19/3418 600/301 |
| 2013/0035871 | A1* | 2/2013 | Mayou .............. | A61B 5/14532 702/26 |
| 2013/0338453 | A1* | 12/2013 | Duke .................. | A61B 5/7282 600/309 |

FOREIGN PATENT DOCUMENTS

| | | | | |
|---|---|---|---|---|
| CN | 103384495 A | | 11/2013 | |
| WO | WO2012/084723 | * | 6/2012 | ............ A16B 5/145 |

* cited by examiner

Fig. 2

METHOD AND DEVICE FOR ANALYZING CONTINUOUSLY MONITORED PHYSIOLOGICAL MEASUREMENT VALUES OF A USER

RELATED APPLICATIONS

This application is a continuation of PCT/EP2014/075833, filed Nov. 27, 2014, which claims priority to EP 13 194 952.1, filed Nov. 28, 2013, both of which are hereby incorporated herein by reference in their entireties.

BACKGROUND

The disclosure relates to a method and a device for analyzing continuously monitored physiological measurement values of a user, a system, and a computer program product.

Such methods and systems are used in order to determine characteristics of patients' measured blood glucose values. The objective is to give the patient as well as the attending medical staff information which enable the patient to deal with his blood glucose values in an improved and appropriate manner.

For people suffering from diabetes, in particular Diabetes Mellitus, it is especially important for them to keep their blood glucose values constantly at a particular level. A precondition for this is knowledge of their blood glucose value which is therefore measured using a blood glucose measuring device set up for this purpose. Blood glucose measuring devices are known in various embodiments.

If it is determined, on the basis of the measured values, that the blood glucose value has exceeded the recommended level, medicine is administered, for example by means of insulin injection or the oral administration of Metformin, an oral antidiabeticum. If the blood glucose values fall below the ideal or recommended level, sugar must be orally ingested, for example through food or drink. If the ideal level is exceeded for an extended period of time, there is the danger of serious health complications such as blindness, kidney damage, limbs having to be amputated or neuropathy. If the exceeding of the prescribed blood glucose level is for a short time only but considerable, this can lead to nausea, dizziness, sweating or even conditions of confusion. Thus, it is particularly important for a diabetic to know his blood glucose values at all times so that he is able to implement the appropriate measures to avoid the blood sugar values deviating from the ideal levels.

A blood glucose measuring device with which the blood glucose values of diabetics can be measured is known, for example from the document DE 10 2004 057 503 A1 and is sold by the applicant under the registered trademark, Accu-Chek.

Blood glucose values for a patient may be determined according to a continuous measurement regime. Such measurements are also known as CGM measurements (Continuous Monitoring blood Glucose Measurement). In this process, the blood glucose values are measured continuously in a continuous time period such that, for example, the progress of the blood glucose value can be collected over an entire day or longer. The analysis of the measured blood glucose values can provide for the determination of several day trends. In this way it is possible to determine blood glucose fluctuations dependent on the time of day.

In connection with the continuous monitoring of blood glucose values, the proposal is made in the document US 2008/0287755 A1, to perform a so-called trend analysis. This can enable the rate of change to be determined on the basis of two or more blood glucose value measurements. The period of continuously monitoring can be between 5 and 30 minutes. Measurement periods of less than 10 minutes or more than 30 minutes can be provided. Within the measurement period, the CGM measurement is performed once per second or once per minute whereby constant or variable cycle lengths can be provided. The known method proposes that the trend thus determined can be presented on a display as a directional arrow.

Further, patterns may be recognized from CGM measurements as shown in WO 2012/084723 A1. Also in WO 2012/076148 A1 systems and methods for automatically displaying patterns in biological monitoring is known.

Furthermore, discontinuous or structured blood glucose measurements are known which are especially also known as SMBG measurements (Self Monitoring Blood Glucose Measurement) and are characterised by the fact that blood glucose values are determined at particular time intervals by means of individual measurements and/or series of measurements. In this way, it is possible, with the help of such blood glucose measurements, which are also known as structured blood glucose measurements, to measure blood glucose values in close proximity to particular events, for example in relation to meals. Disadvantages of structured blood glucose measurement can arise if events relevant for the blood glucose value of the diabetic occur between the measurement times so that they are undetectable. In the document US 2009/0054753 A1, a procedure is described whereby an individual blood glucose measurement in the scope of a discontinuous measurement is used to determine the time for a subsequent further individual measurement according to certain parameters. The parameters take into account patient and environmental conditions.

Document US 2012/0289788 A1 discloses a method for determining and evaluating measurement values. Data streams of measurement values can be compared with each other and in reference to a set of control parameters. If a data stream deviates from its control parameters, a query is sent to a mood sensor for requesting an input of a mood of a user.

Document US 2012/0232520 A1 discloses a method and a system for detecting an analyte sample. Stored measurement values are evaluated in order to make a proposal for a recommended drug dosage. A request is made to a user for asking whether a hypoglemic event had occurred. This information is taken into account for adopting the recommended dosage, but not stored in the system.

SUMMARY

This disclosure teaches improved technologies for analyzing continuously monitored physiological measurement values of a user.

According to one aspect, a method for analyzing continuously monitored physiological measurement values of a user is provided, especially continuously monitored blood glucose values. The method is performed in a data processing system. The data processing system may be implemented in a device for continuously collecting and/or analyzing physiological measurement values for use of, for example, blood glucose values. As an alternative, the data processing system may be provided by a general computer system which is connectable to the measurement device for data transmission.

In the course of the method a set of present physiological measurement values collected in a continuously performed present measurement is provided by a data interface. The measurement values may be continuously measured blood glucose values for a patient or user. It is determined whether a common pattern of values is contained in both the set of present physiological measurement values and a set of historical physiological measurement values collected in a continuously performed historical measurement. The determining electronic pattern information for both the set of present physiological measurement values and the set of historical physiological measurement values may be analyzed.

A pattern recognition process may be used for determining whether the pattern of values determined from the one of the sets of physiological measurement values, e.g., the present physiological measurement values, is contained in the other set of physiological measurement values, e.g., the historical physiological measurement values. Different implementations for the process of determining one or more patterns from a set of measured values and comparing patterns as such are known. In this respect reference is made, for example, to WO 2012/084723 A1 and WO 2012/076148 A1. Within the scope of the present disclosure, a pattern is, in general, understood to be a sequence of measurement values. In a simple case, the present pattern determined for the present data may correspond to the set of values collected over a time period, e.g., three or four hours, till now. Accordingly, a comparison pattern should be understood to be a sequence of measurement values that were acquired during a comparison time interval. The comparison time interval is understood to mean a time interval that is, or could be, of interest for the analysis of the physiological measurement values.

If the common pattern of values is found to be contained in both the set of present or current physiological measurement values and the set of historical physiological measurement values, the user is requested to provide contextualization for at least the present physiological measurement values of the pattern of values via a user IO-device (IO—input/output) of the data processing system. The patterns of values in the historical physiological measurement values on one side and the present physiological measurement values on the other side have not to be identical. It may also be that it is decided to have found the pattern of values determined from one of the set of present or current physiological measurement values and the set of historical physiological measurement values in the other measurement values if the present and the historical patterns are comparable (resemble) to a certain extent. For example, there may be pattern identity to an extent of about 80%. In such case, for example, only 80% of the physiological measurement values may be comparable with respect to time difference between the measurement values and value level difference.

Contextualization for at least the present physiological measurement values belonging to the common pattern of values determined in the set of present physiological measurement values is received from a user input via the IO-device, and contextualized data are stored for at least the present physiological measurement values of the common pattern of values in a storing device of the data processing system. Contextualization may be received and stored for all of present physiological measurement values or part of it.

According to another aspect, a device for analyzing continuously monitored physiological measurement values of a user, especially continuously monitored blood glucose values, is provided. The device comprises a data processing system which is configured to perform steps of:

providing, by a data interface, a set of present physiological measurement values collected in a continuously performed present measurement, determining whether a common pattern of values is contained in both the set of present physiological measurement values and a set of historical physiological measurement values collected in a continuously performed historical measurement, if the common pattern of values is found to be contained in both the set of present physiological measurement values and set of historical physiological measurement values, requesting the user to provide contextualization for at least the present physiological measurement values of the common pattern of values via a user IO-device of the data processing system, receiving contextualization for at least the present physiological measurement values of the common pattern of values from a user input via the IO-device, and storing contextualized data for at least the present physiological measurement values of the common pattern of values in a storing device of the data processing system.

According to still another aspect, a computer program product is provided, preferably stored on a non-transitory storage medium, and configured to perform the method for analyzing continuously monitored physiological measurement values of a user.

Among other advantages, by the technologies proposed it is ensured that the present or current physiological measurement values are stored correctly contextualized. The amount of measurement data collected by CGM measurements can be stored in a favourable way for subsequent data analysis. Non correct data collection due to user fault is avoided. The base for subsequent measurement value analysis is created with higher reliability.

Pattern matching is linked to other system functions, such as a prompt for additional data input, e.g., by the user, pattern recognition may be made more efficient. In this way, a self-learning system may be provided that recognizes an assigned event.

The step of determining may further comprise: determining a present pattern of values is contained in the set of present physiological measurement values, providing electronic pattern information about a historical pattern of values determined from a set of historical physiological measurement values, and determining the presence of the common pattern if the present pattern and the historical pattern resemble. Prior to the step of determining the presence of the common pattern, either the present or the historical pattern of values may be determined first. The process of determining may be repeatedly performed during an ongoing present physiological measurement. Each time the present pattern of values may be measurement time window covering a fixed or dynamically changing time period of continuous measurement. The measurement time windows of consecutive analysis steps may overlap. Contextualization of the present measurement values is continuously ensured.

The step of requesting may further comprise outputting a pre-selection of proposed contextualization data. Contextualization as whole may be user input. As an alternative, a pre-selection of proposed contextualization data may be provided to the user, for example, by outputting such pre-selection over a display device. The user may just confirm the pre-selection without amending the proposed contextualization. Also, the user may amend the proposed contextualization by adding and/or deleting contextualization data.

The outputting may comprise outputting a pre-selection of proposed contextualization data determined from contextualization of the common pattern of values determined in the set of historical physiological measurement values. The content of the proposed contextualization, at least in part, may be taken from the contextualization assigned to the historical physiological measurement values. The contextualization assigned to the historical physiological measurement values may be included in the proposed contextualization data as whole or in part. In the data processing system, the pre-selection of proposed contextualization data may be provided together (at the same time) with electronic pattern information about the pattern of values determined from the set of historical physiological measurement values.

The step of outputting may further comprise outputting the pre-selection of proposed contextualization data with a data format determined from the contextualization of the common pattern of values determined in the set of historical physiological measurement values. The data format is derived from the historical physiological measurement values. The data format determined is used for the pre-selection of proposed contextualization data. For example, the data format defines the kind of context information which is required. The contextualized data for at least the present physiological measurement values of the pattern of values may be stored using the same or a different data format in the storing device.

The outputting may further comprise steps of determining a type of pattern for the common pattern of values contained in both the set of present physiological measurement values and the set of historical physiological measurement values, and outputting a pre-selection of proposed contextualization assigned to the type of common pattern determined. The type of pattern may be distinguished by one or more parameters. For example, different types of patterns may be distinguished by a parameter selected from the following group: number of measurement values included, time interval covered by the pattern, and event indicated by the pattern of values. Depending on the type of the pattern of values a certain pre-selection of proposed contextualization may be selected from a data base containing different sets of proposed contextualization representing different pre-selections.

The contextualization data may comprise information selected from the following group: time of measurement, take of carbon hydrates, type of exercise, type of event, illness, medication, stress, menstruation, and insulin bolus.

If the common pattern of values and the contextualization for both the historical physiological measurement values and the present physiological measurement values compare to each other (resemble), future continuous physiological measurement values may be predicted and displayed. The predicted values may represent an expected trend or course of the physiological value, e.g., the blood glucose level of the user or patient (blood glucose level forecast).

The displaying may comprise displaying a level of confidence of the prediction of the future continuous physiological measurement values. The reliability of a physiological value level forecast can be determined on the basis of pattern matching and context data. If matching between one or more patterns in both the historical and the present physiological values is determined and if, in addition, a high degree of matching also exists between the context data, the forecast physiological value may be displayed with an indicator indicating a high confidence/reliability level. It enables the physiological value trend to be forecast on the basis of historical measurement data and pattern recognition. Unlike in the art, this entails using not only the pattern recognition of the physiological value trend as such but also the matching of the context data for the pattern in question. Consequently, it is thus possible to output a probability/reliability value for the forecast based on physiological values and the context thereof. If both the pattern of values recognized in the historical und the present physiological values and the contextualization data provided for at least the historical und the present physiological values of the pattern of values are identical the highest level of confidence, e.g., a 100% indicator or an indicator of a certain color (e.g., dark green), is displayed to the user. A lower level of confidence is indicated, e.g., by a light green indicator, in case one of the pattern of values and the contextualization data don not match perfectly.

The data processing system may be provided in a blood glucose control device configured to continuously monitor the blood glucose level of a user. As outlined above, different embodiments for blood glucose control device as such are known in the art.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following description. Rather, the embodiments are chosen and described so that others skilled in the art may appreciate and understand the principles and practices of this disclosure.

Figure 1:
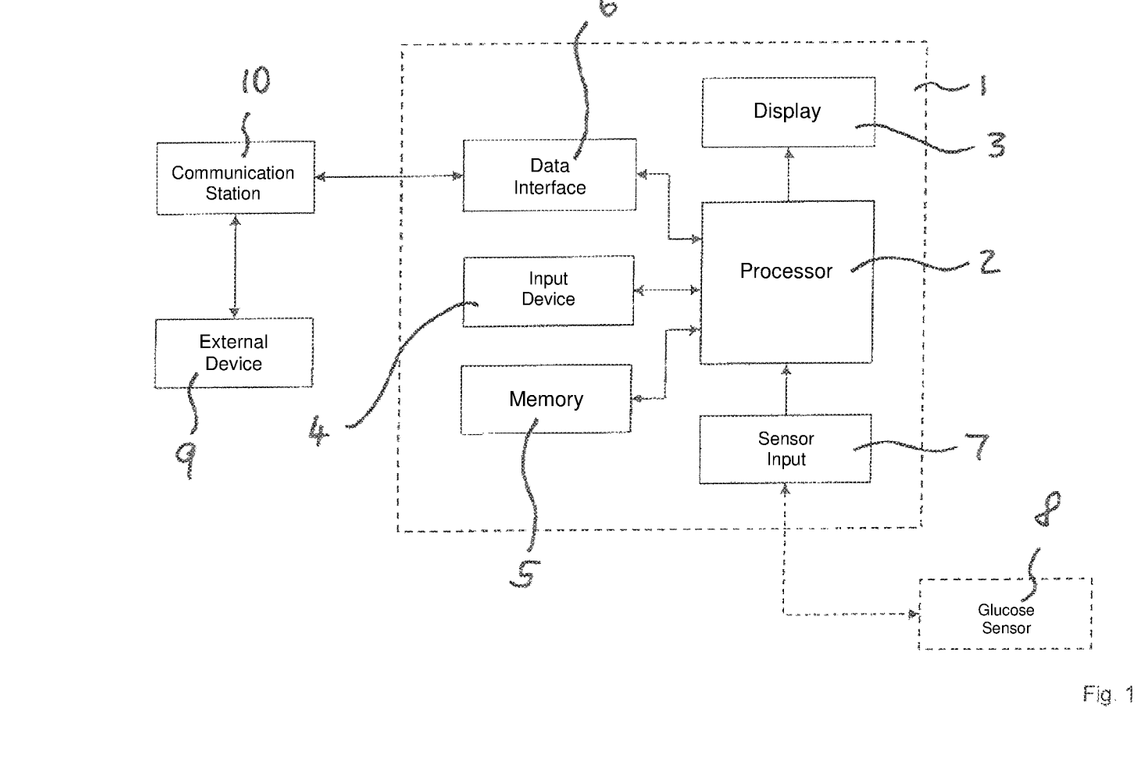
FIG. 1 is a schematic representation of a system for performing a method for analyzing continuously monitored physiological measurement values of a user.

FIG. 1 is a schematic representation of a device or apparatus 1 for analyzing continuously monitored physiological measurement values of a user. In the embodiment shown the device 1 which is provided with a data processing system may be configured for a mode of continuously measuring blood glucose values. The device 1 may be a mobile or handheld device such as a mobile personal computer, a glucose meter or a mobile smart phone. Also, the device 1 may be a desktop device, e.g., a desktop computer. The device 1 is provided with a processor 2 which is connected for data exchange with a display device 3, an input device 4 such as a keypad, a memory 5, and a data interface 6. Some of those elements provide for IO components (IO—input/output) such as the display device 3, the input device 4, and the data interface 6.

In the embodiment shown in FIG. 1, the device 1 comprises a sensor input 7 connectable to a glucose sensor device 8. The sensor input 7 and the glucose sensor device 8 are provided optionally, e.g., in the case that the device 1 is implemented by a continuous glucose meter. The glucose sensor device 8 employs a sensor that produces a measured glucose level of the user or produces a signal that corresponds to a measured glucose level of the user. The glucose sensor device 8 communicates these signals to the device 1 that may be designed to interpret these signals to produce a characteristic reading or value for the user, i.e., a measurement of the characteristic. The sensor signals enter the device 1 through the sensor input 7 and through the sensor input 7 the signals are conveyed to the processor 2. If such embodiment is provided, the processor 2 may determine and manipulate the sensor readings.

In addition, the device 1 may provide additional functions that will aid in the treatment regime to which the characteristic reading applies. For example, but not limited to, the device 1 may track meals, exercise and other activities which affect the treatment of diabetes.

Other components of the device 1 support the processor 2 in performing functions. The memory 5 is used to store data and instructions used by the processor 2. Also, the memory 5 may be used for storing historical and/or present continuously monitored physiological measurement values such as continuously monitored blood glucose values.

The input device 4 which may comprise a keypad is used to receive direct input from the user and the display device 3 such as a liquid crystal display (LCD), or the like, is used to output information to the user. The data interface 6 may be provided with a digital input/output port.

The data interface 6 can be used for the device 1 to communicate with an external device 9 such as a computer. To facilitate communication, the device 1 may interface with the external device 9 through a communication station 10 that can serve a docking station for the device 1, for example. In some embodiments, the data interface 6 within the characteristic monitoring apparatus 1 may be directly connected to the external device 9. Through the communication link, data may be downloaded from the device 1. Thus, advanced analysis can be performed on a computer freeing the memory 5 within the device 1. Data such a characteristic settings and programs can also be downloaded to the device 1. In this way, the device 1 can be conveniently reprogrammed without requiring manual entry by the user. Especially, continuously measured blood glucose values may be received by the device 1.

Following, further aspects of a method for characteristic monitoring in conjunction with a mode of continuously measured blood glucose (CGM) values are described.

CGM value data are received in the device 1, e.g., through the data interface 6. The CGM data shall be contextualised with further background information. The CGM data are to be used for the event specific support of the user in everyday decisions. This support may include the automatic generation of information for the user relating to current actions and evaluations of the current metabolic situation ("advice"), as well as information about future situations ("forecast") and their evaluation, and also information about how a negative development can be prevented through taking early action. The user may be kept up to date by way of alarms and/or reminders. The relevant metabolic situations may be shown in a suitable graphic form through highlighting etc. and/or also through other suitable response mechanisms such as visual and/or acoustic signals.

Figure 2:
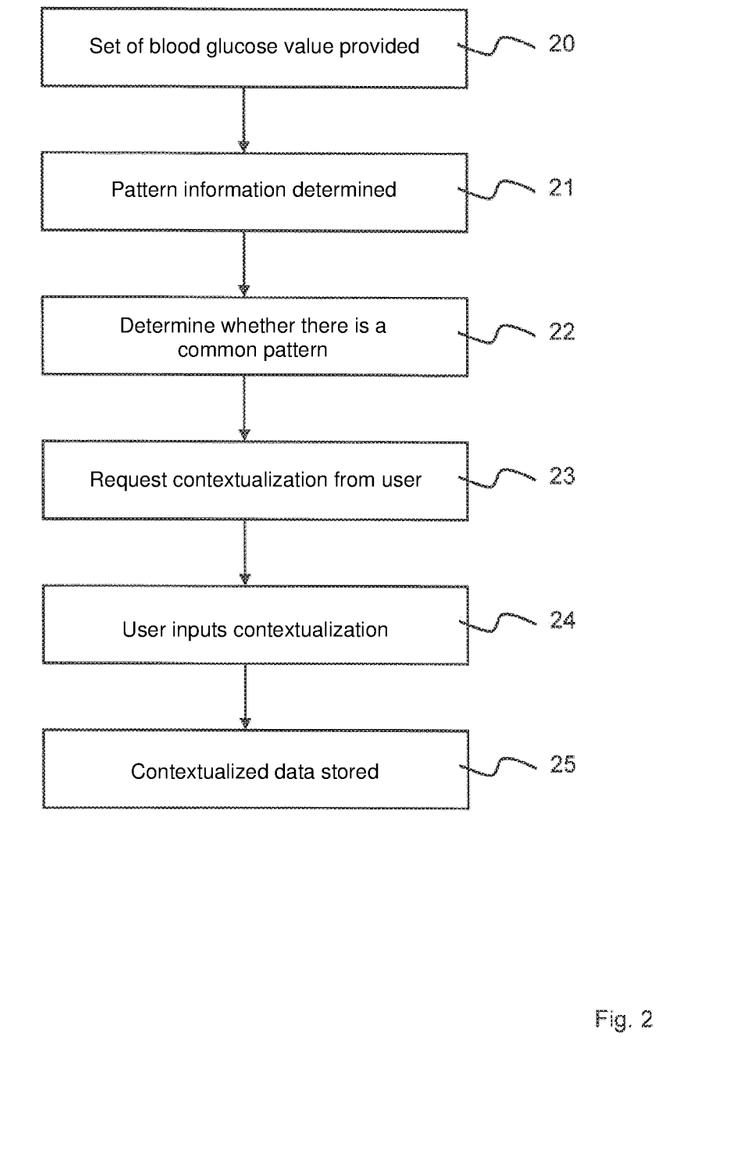
FIG. 2 is a block diagram of an embodiment of a method for analyzing continuously monitored physiological measurement values of a user.

FIG. 2 shows a block diagram of an embodiment of a method for analyzing continuously monitored physiological measurement values of a user. The method may be implemented by using the device 1 shown in FIG. 1.

In a step 20, a set of present or current blood glucose values collected in a continuously performed present measurement (CGM value data) is provided. According to one embodiment, in a step 21, pattern information, namely a present pattern of values, is determined for set of present or current blood glucose values. In a simple embodiment, the present pattern of values may resemble the whole set of present blood glucose values collected over a past time period till the time of determining the common pattern. Following, in step 22, by means of the processor 2 it is determined whether there is a common pattern of values in both the set of present physiological measurement values and a set of historical physiological measurement values collected in a continuously performed historical measurement for which electronic information is provided to the processor as well. The electronic information comprises pattern information indicating one or more pattern of values contained in the historical blood glucose values. The step of determining the presence of a common pattern of values comprises pattern recognition providing for identification of a pattern of values identified for one set of measurement values in another set of measurement values.

A step for identifying one or more historical patterns in the set of historical blood glucose values may be performed after and/or while the present pattern is determined for the present blood glucose values.

If it is determined that there is a common pattern of values contained in both the set of present and the set of historical blood glucose values, in step 23 the user is requested to provide contextualization for at least the present physiological measurement values of the pattern of values via the display device 3. A pre-selection of contextualization data may be presented to the user on the screen of the display device 3. Such pre-selection of contextualization data may be determined from the historical blood glucose values contextualized before. The user may amend the contextualization data presented. The user may add further contextualization data to the data presented as the pre-selection. Also, the user may disregard the pre-selection of contextualization data in part or even completely and provide its own contextualization data.

Pattern recognition or pattern matching enables known patterns in physiological measurement data, e.g., CGM measurement data, to be recognized automatically. In particular, it may serve to reveal a historical situation of the user that matches the user's current situation as closely as possible, so that appropriate measures may be taken according to the case (see for example WO 2012/084723 A1). Similarly, automatic event recognition by clustering of patterns taking account of time is disclosed in WO 2012/076148 A1.

After receiving contextualization for at least the present blood glucose values of the pattern of values from the user input in step 24, the contextualized data for at least the present blood glucose values of the pattern of values are stored in the memory 5 in step 25. In addition or as an alternative, the present blood glucose values together with contextualized data may be outputted via the data interface 6.

In most cases, patterns in measured values are identified with reference to an automatically or manually entered contextualization such as the time, day and possibly meal tags. Unfortunately, the contextualization is often absent or incomplete, which constitutes a hindrance to interpretation of the pattern. Furthermore, the reliability of the pattern recognition is not always adequate.

By the technologies proposed here, pattern recognition is carried out initially with reference to historical data. In this context, the pattern recognition may be based not only on past blood glucose values but also on context data associated with the historical blood glucose values, if such data is available. If a pattern determined from the present or the historical measurement data is recognized in the other blood glucose measurement values, the user is automatically prompted to contextualize the present measurement data. The system advantageously may provide a pre-selection of a possible context automatically on the basis of the historical data. Accordingly, all the user may have to do is confirm the entry of a context, and he is thus spared the task of carrying out additional data input steps.

Unlike in the art, in which a missed bolus may be recognized on the basis of a significant change in the real-time glucose values, the solution proposed here enables a context to be recognized. This therefore makes it possible for automatic event recognition to be performed. This also enables recognition of complex situations in the measurement data in which multiple events are coincident. Finally, the system is able to learn to fully automate a data entry at least for regularly occurring situations/events depending on the available historical data.

In addition, the reliability of a blood glucose level forecast can be calculated on the basis of pattern matching and context data. If the match between patterns in the historical and the present blood glucose values is close and if a high degree of matching also exists between the context data for example, the forecast blood glucose value is displayed with a high confidence/reliability level. Accordingly, a further aspect is that it enables the blood glucose trend to be forecast on the basis of historical measurement data and pattern recognition. Unlike in the art, this entails using not only the pattern recognition of the blood glucose trend as such but also the matching of the context data for the pattern in question.

Consequently, it is thus possible to output a probability/reliability value for the forecast based on glucose values and the context thereof. For example, if the system detects a match of x %, e.g., 60 or 70%, in the blood glucose trend, and if the context data of the blood glucose values also exhibit a high matching percentage, greater confidence may be placed in the reliability of the blood glucose level forecast than if the glucose data manifests a high level of matching but not the context data. Accordingly, the technologies presented may be implemented advantageously in a CGM system that displays a forecast of the glucose trend and at the same time also displays the reliability of the forecast. If the forecast is within a "green zone" for example, the user may thus optionally dispense with further blood glucose measurements. It is thus conceivable that the system or device may assign the forecast to various categories (uncertain, probable, very certain), and in this case further criteria, e.g., threshold values/ranges for the glucose value, the curve gradient and so on, may also be taken into account.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method for analyzing continuously monitored glucose measurement values of a user, the method being performed in a data processing system and comprising:
   providing, by a data interface, a set of present glucose measurement values collected in a continuously performed present measurement;
   determining whether a common pattern is contained in both the set of present glucose measurement values and a set of historical glucose measurement values collected in a continuously performed historical measurement; and
   when the common pattern is found to be contained in both the set of present glucose measurement values and the set of historical glucose measurement values:
   a) requesting the user to provide context data for at least the present glucose measurement values of the common pattern via a user input/output device ("IO-device") of the data processing system;
   b) receiving the context data for at least the present glucose measurement values of the common pattern via the IO-device;
   c) storing the context data for at least the present glucose measurement values of the common pattern in a storing device of the data processing system;
   d) comparing the context data for the present glucose measurement values to context data of the historical glucose measurement values;
   e) when it is determined in step d) that the present context data resembles the historical context data, predicting a future glucose measurement value based on the historical glucose measurement values that follow the common patter;
   f) using the comparison between the context data for the present glucose measurement values and the context data of the historical glucose measurement values to determine a confidence level for the predicted future glucose measurement value; and
   g) administering insulin when the predicted future glucose measurement value exceeds a recommended level.

2. The method according to claim 1, wherein the determining of whether a common pattern is contained in both the set of present glucose measurement values and the set of historical glucose measurement values further comprises:
   determining a present pattern of values in the set of present glucose measurement values;
   providing electronic pattern information about a historical pattern of values determined from the set of historical glucose measurement values; and
   determining the presence of the common pattern if the present pattern resembles the historical pattern.

3. The method according to claim 1, wherein the requesting in step a) further comprises outputting a pre-selection of proposed context data.

4. The method according to claim 3, wherein the outputting comprises outputting a pre-selection of proposed context data determined from context data of the historical glucose measurement values from the common pattern.

5. The method according to claim 3, wherein the outputting further comprises outputting the pre-selection of proposed context data with a data format determined from the context data of the historical glucose measurement values from the common pattern.

6. The method according to claim 3, wherein the outputting further comprises: determining a type of pattern for the common pattern contained in both the set of present glucose measurement values and the set of historical glucose measurement values; and outputting the pre-selection of proposed context data assigned to the type of pattern determined.

7. The method according to claim 1, wherein the context data comprises information selected from the following group: time of measurement, intake of carbohydrates, type of exercise, type of event, illness, medication, stress, menstruation, and insulin bolus.

8. The method according to claim 1, wherein the confidence level for the predicted future glucose measurement value is displayed.

9. The method according to claim 1, wherein the data processing system is provided in a blood glucose control device configured to continuously monitor the blood glucose level of a user.

10. A non-transitory computer-readable medium having embodied thereon computer-executable instructions, which when executed by a data processing system, cause the system to perform the method according to claim 1.

11. The method according to claim 1, further comprising using a glucose sensor to continuously monitor blood glucose values of the user and to collect the set of present glucose measurement values.

12. The method according to claim 11, further comprising using the glucose sensor to continuously monitor blood glucose values of the user and to collect the set of historical glucose measurement values.

13. The method according to claim 1, wherein the requesting of the user to provide context data comprises displaying a request on a screen.

14. The method according to claim 1, wherein the receiving context data step comprises the user inputting into a keyboard.

15. The method of claim 1, wherein the confidence level for the predicted future glucose measurement value is a function of the degree of matching of the present context data and the historical context data.

\* \* \* \* \*

UNITED STATES PATENT AND TRADEMARK OFFICE
CERTIFICATE OF CORRECTION

PATENT NO. : 10,791,993 B2
APPLICATION NO. : 15/166413
DATED : October 6, 2020
INVENTOR(S) : Bernd Steiger and Jürgen Rasch-Menges Page 1 of 1

It is certified that error appears in the above-identified patent and that said Letters Patent is hereby corrected as shown below:

In the Claims

Claim 1, Column 10, Line 6, the phrase "TO-device" should read --IO-device--.

Claim 1, Column 10, Lines 21-22, the phrase "that follow the common patter" should read --that follow the common pattern--.

Signed and Sealed this
Twelfth Day of January, 2021

Andrei Iancu
*Director of the United States Patent and Trademark Office*